(12) United States Patent
Palmer et al.

(10) Patent No.: US 8,431,749 B2
(45) Date of Patent: Apr. 30, 2013

(54) RECOVERY OF PHENOL AND ACETONE FROM BISPHENOL-A STREAMS

(75) Inventors: David P. Palmer, Katy, TX (US); Steven D. Evitt, Somerville, MA (US); Stephen W. Fetsko, Hingham, MA (US); Chung-Ming Chi, Needham, MA (US)

(73) Assignee: Badger Licensing LLC, Cambridge, MA (US)

( * ) Notice: Subject to any disclaimer, the term of this patent is extended or adjusted under 35 U.S.C. 154(b) by 120 days.

(21) Appl. No.: 13/153,909

(22) Filed: Jun. 6, 2011

(65) Prior Publication Data

US 2012/0310015 A1    Dec. 6, 2012

(51) Int. Cl.
- *C07C 45/78* (2006.01)
- *C07C 37/68* (2006.01)
- *C07C 37/20* (2006.01)

(52) U.S. Cl.
USPC .................... 568/386; 568/724; 568/753

(58) Field of Classification Search .......... 568/386, 568/749, 724, 753
See application file for complete search history.

(56) References Cited

U.S. PATENT DOCUMENTS

| 3,075,015 A | 1/1963 | Meyer et al. |
| 6,191,316 B1 | 2/2001 | Fennhoff et al. |
| 2006/0004234 A1 | 1/2006 | Prein et al. |

FOREIGN PATENT DOCUMENTS

| EP | 0112615 A2 | 7/1984 |
| GB | 795236 A | 5/1958 |

OTHER PUBLICATIONS

Adschiri T., Shibata R., Arai, K., Sekiyu Gakkasishi, "Phenol Recovery by BPA Tar Hydrolysis in Supercritical Water", vol. 40, No. 4, 1997, p. 291-297.
International Search Report and Written Opinion of the International Searching Authority issued in a corresponding PCT/US2012/040680 on Aug. 31, 2012.

*Primary Examiner* — Sikarl Witherspoon
(74) *Attorney, Agent, or Firm* — Roberts Mlotkowski Safran & Cole, P.C.

(57) ABSTRACT

In a method of recovering phenol and acetone from a feed stream containing bisphenol-A and isomers thereof, the feed stream is contacted with water and a source of hydroxyl ions under conditions effective to decompose at least part of said bisphenol-A and isomers thereof to phenol and acetone. The conditions include a temperature of about 150° C. to about 300° C., a pressure sufficient to keep the water substantially in the liquid phase at said temperature, and a molar ratio of hydroxyl ions to hydroxyphenyl groups in the residue stream from about 0.3:1 to about 0.9:1.

15 Claims, 4 Drawing Sheets

RECOVERY OF PHENOL AND ACETONE FROM BISPHENOL-A STREAMS

FIELD

The present invention relates to the recovery of phenol and acetone from bisphenol-A streams and particularly bisphenol-A residue streams.

BACKGROUND

Bisphenol-A (4,4'-dihydroxy-2,2-diphenylpropane or BPA) is produced by condensation of acetone with an excess of phenol in the presence of an acidic catalyst or a cation-exchange resin. The crude product, in addition to the desired bisphenol-A and unreacted phenol, contains unwanted by-products, such as bisphenol-A isomers, trisphenols and other higher molecular weight materials. The bisphenol-A is normally separated from the crude product by a single or a series of crystallization steps, leaving a mother liquor stream enriched in unwanted by-products, a portion of which stream is removed to purge unwanted by-products from the process. Alternately, the bisphenol-A may be separated from the crude product by a single or series of distillation steps, which also creates a stream enriched in unwanted by-products, a portion of which is removed. The removed stream may contain unreacted phenol and bisphenol-A as well as the unwanted by-products. Phenol is typically recovered from the removed stream by distillation, normally vacuum distillation, leaving a residue stream concentrated in unwanted heavies which is purged from the BPA manufacturing process.

There is substantial prior art describing methods for recovering phenol and isopropenyl phenol from such residue streams to improve the economic performance of the overall BPA manufacturing process. One such method involves addition of catalytic amounts of base at elevated temperature under vacuum to decompose BPA, BPA isomers, trisphenols and other by-products into phenol and isopropenyl phenol followed by addition of catalytic amounts of acid at elevated temperature under vacuum to recover phenol (see, U.S. Pat. No. 6,191,316).

In addition, there is substantial prior art describing methods for recovering phenol and acetone from BPA and BPA residue streams. One such method involves hydrolysis of BPA residues purged from a BPA manufacturing process in the presence of water at supercritical or near-supercritical temperatures and pressures (see, "Phenol Recovery by BPA Tar Hydrolysis in Supercritical Water", Adschiri T., Shibata R., Arai, K., Sekiyu Gakkasishi, Vol 40, No. 4, 1997, p. 291-297).

Moreover, hydrolysis of BPA and BPA residues has been shown to occur at subcritical temperatures and pressures in the presence of an aqueous solution of ammonia, alkali-metal and alkaline earth metal hydroxides and carbonates to produce phenol and acetone which can then be recovered (see, U.S. Pat. No. 3,075,015). In this process, the hydrolysis is conducted at a temperature of 150° C. to 320° C., such as 200° C. to 300° C., a pressure of 5 to 150 atmospheres and, in each of the Examples, at a molar ratio of hydroxyl to hydroxyphenyl groups of 1:1. The concentrated heavies are reacted with sodium hydroxide solution or other basic solution to convert the p,p-BPA and other compounds back to phenol and acetone. The acetone is recovered in a distillation column and the phenol is recovered by neutralization followed by steam distillation. Phenol and acetone yields using hydrolysis are substantially improved compared to methods using catalytic decomposition in the absence of water, but the caustic usage is high.

According to the present invention it has now been found that BPA-containing streams can be effectively hydrolyzed back to phenol and acetone in the presence of a basic hydroxide at molar ratios of hydroxyl to hydroxyphenyl groups significantly less than 1:1 and with relatively short residence times. In addition, it is found that acetone and phenol recovery rates increase as the ratio of water to concentrated heavies in feed stream increases. In this way, the efficiency of the process can be maximized while the caustic usage and hence cost of the process is reduced.

SUMMARY

In one aspect, the invention resides in a method of recovering phenol and acetone from a feed stream containing bisphenol-A and isomers thereof, the method comprising contacting the feed stream with water and a source of hydroxyl ions under conditions effective to decompose at least part of said bisphenol-A and isomers thereof to phenol and acetone, said conditions including a temperature of about 150° C. to about 300° C., a pressure sufficient to keep the water substantially in the liquid phase at said temperature, and a molar ratio of hydroxyl ions to hydroxyphenyl groups in the residue stream from about 0.3:1 to about 0.9:1.

Conveniently, said temperature is 180° C. to about 260° C. and the molar ratio of hydroxyl ions to hydroxyphenyl groups in said feed stream is from about 0.4:1 to about 0.7:1.

Conveniently, said contacting is conducted for a time less than 4 hours, such as for about 2 to about 3 hours.

In one embodiment, the feed stream is a residue stream from the production of bisphenol-A, containing unreacted phenol, BPA, BPA isomers, trisphenols and other heavy aromatic compounds. Conveniently, weight ratio of water to the sum of BPA, BPA isomers, trisphenols and other aromatic heavies in the feed stream is greater than or equal to 2:1, for example from about 2:1 to about 10:1.

In a further aspect, the invention resides in a method of producing bisphenol-A, the method comprising:

(a) condensing acetone with a molar excess of phenol in the presence of a catalyst under conditions to produce a product stream comprising bisphenol-A and isomers thereof, unreacted phenol, trisphenols and other heavy aromatic compounds;

(b) recovering part of the bisphenol-A and unreacted phenol from said product stream to leave a residue stream comprising unreacted phenol, BPA, BPA isomers, trisphenols, and other heavy aromatic compounds;

(c) contacting the residue stream with water and a source of hydroxyl ions at a temperature of about 150° C. to about 300° C. and a pressure sufficient to keep the water substantially in the liquid phase at said temperature, wherein the molar ratio of hydroxyl ions to hydroxyphenyl groups in the residue stream is from about 0.3:1 to about 0.9:1 and wherein the contacting hydrolyzes the residue stream to produce an effluent stream containing phenol and acetone; and (d) recovering phenol and acetone from the effluent stream.

DETAILED DESCRIPTION OF THE EMBODIMENTS

Figure 1:
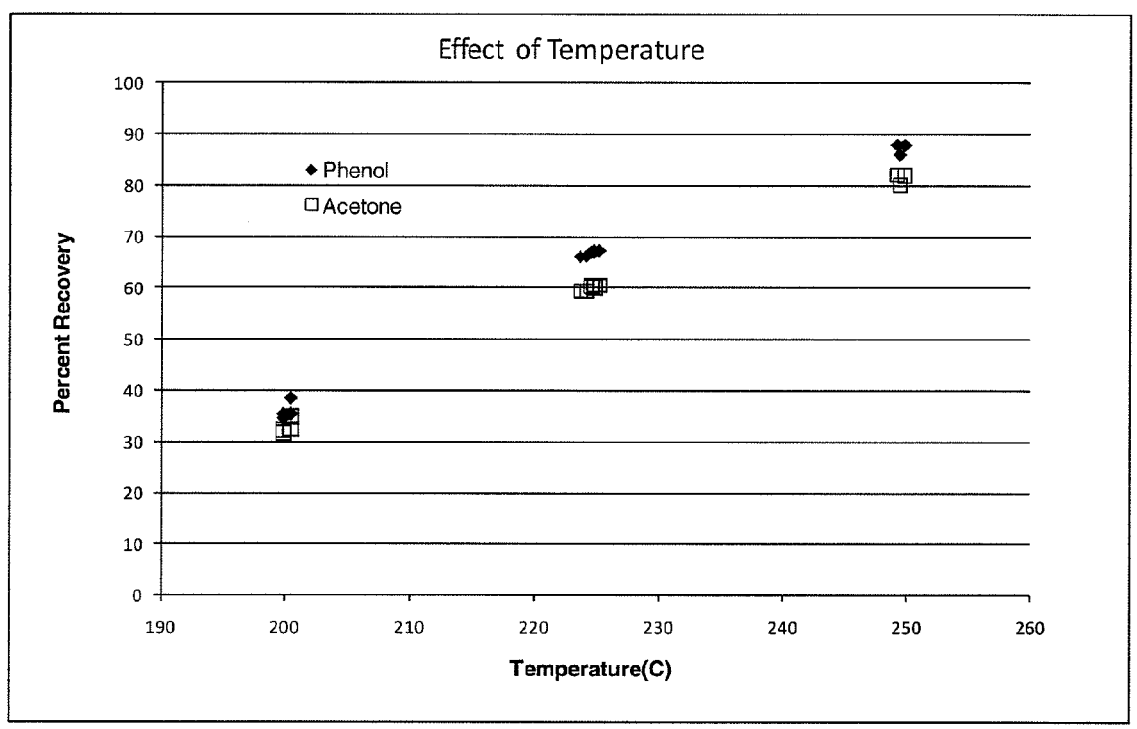
FIG. 1 is a graph of wt % phenol and acetone recovery against temperature in a process for treating a BPA residue stream with an aqueous NaOH solution according to Example 1.

Described herein is an improved process for recovering phenol and acetone from a feed stream containing isomers of bisphenol-A (BPA). Although the feed can be any stream containing BPA and/or the isomers thereof found in a BPA manufacturing plant, in most cases the feed will be a residue stream remaining after part of the BPA and unreacted phenol have been separated from the effluent stream of the condensation of acetone with phenol.

The manufacture of bisphenol-A (BPA) generally involves reacting acetone with a stoichiometric excess of phenol in the presence of an acid catalyst. The phenol/acetone molar ratio is usually in the range from 3 to 30, typically from 5 to 20. The reaction is typically carried out at a temperature of about 50 to about 100° C. under a pressure of from atmospheric pressure to about 600 kPa.

As the catalyst, usually strong mineral acids or strongly acidic cation exchange resins such as sulfonic acid type resins, including those partially neutralized with a sulfur-containing amine compound are used. As the sulfur-containing amine compound, ordinary promoters used for the synthesis of bisphenol A such as, for example, 2-(4-pyridyl)ethanethiol, 2-mercaptoethylamine, 3-mercaptopropylamine, N,N-dimethyl-3-mercaptopropylamine, N,N-di-n-butyl-4-mercaptobutylamine, and 2,2-dimethylthiazolidine can be used. Such a promoter is used in an amount of usually 2 to 30 mol %, such as 5 to 20 mol % based on the acid group (sulfonic group) in the acid ion exchanger.

The condensation reaction of the phenol and acetone is typically conducted in a fixed bed continuous flow system or a suspended bed batch system. In the case of the fixed bed flow system, the liquid space velocity of the mixture of the raw materials supplied to the reactor is usually 0.2 to 50 $hr^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

In addition to the desired bisphenol-A, the effluent from the condensation reaction comprises reaction-generated water, unreacted acetone, unreacted phenol, and a variety unwanted by-products, such as bisphenol-A isomers (for example, 2-(4-hydroxyphenyl)-2-(2-hydroxyphenyl)propane or o,p-BPA), trisphenol (see formula I below), isopropenyl phenol (IPP) dimers (see formulae IIa, IIb and IIc below) and hydroxyphenyl chromans (see formulae IIIa and IIIb below), substituted xanthenes and more highly condensed compounds having three or more phenyl rings in the molecular framework. Collectively, the IPP dimers, hydroxylphenyl chromans, indanes, xanthenes and more highly condensed compounds are termed as "BPA heavies."

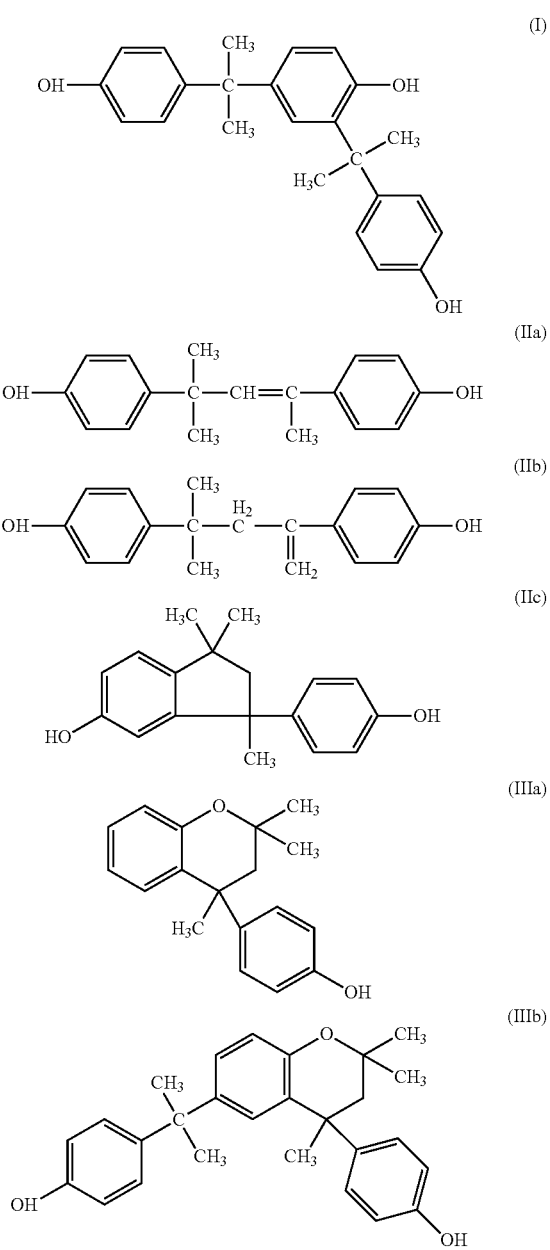

These by-products, as well as the water, unreacted phenol and unreacted acetone, impair the suitability of the BPA for the production of polymers and must be separated from the condensation effluent. For the production of polycarbonate in particular, high demands are made on the purity of the raw material BPA.

The purification of the BPA is carried out by a multi-stage cascade of suitable purification processes such as, for example, suspension crystallization, melt crystallization, distillation and/or desorption. After separation of the BPA product, these processes leave a mother liquor which contains BPA, water, unreacted phenol and possibly unreacted acetone, and which is rich in the above-mentioned by-products. Typically, this stream of mother liquor is recycled to the condensation reaction. In order to maintain the catalytic activity of the acidic ion exchanger, all or some of the water that has formed is removed beforehand by distillation, together with any unreacted acetone that is still present. The dewatered mother liquor so obtained is supplemented with additional phenol and acetone and fed back into the condensation unit.

Such a recycle procedure has the disadvantage that the by-products of the BPA preparation become concentrated in the circulating stream and can adversely affect the purity of the final BPA product and may lead to deactivation of the catalyst system. In order to avoid excessive concentration of the by-products in the circulating stream, a portion of the mother liquor mixture must be discharged from the system. The discharge is typically effected by removing a portion of the mother liquor from the circulating stream, often after distillation to remove water of reaction, unreacted acetone and part of the unreacted phenol. The composition of the mother liquor at this point, and accordingly also the composition of the discharge, typically comprises from 60 to 90 wt. % phenol, from 6 to 20 wt. % BPA and from 3 to 15 wt. % BPA isomers and heavier by-products. Since this discharge stream contains significant quantities of phenol and other useful products, the discharge is a valuable process stream which is subjected to further processing.

Further processing of the discharge stream initially involves distilling off the phenol to a residual content of less than 20 wt %, such as less than 10 wt. %, especially less than 5 wt. %, even less than 1 wt. %, normally by vacuum distillation, leaving a heavy residue stream comprising <10 wt. % phenol, from about 45 to about 55 wt. % BPA and from about 45 to 55 wt. % BPA heavies.

After removal of the phenol, the heavy residue stream is contacted with water and a source of hydroxyl ions under conditions effective to decompose at least part of the residue stream to phenol and acetone. Suitable conditions for hydrolysis of the residue stream include a temperature of about 150° C. to about 300° C., such as about 180° C. to about 260° C., at a pressure sufficient to keep the water substantially in the liquid phase at said temperature. Suitable pressures are from about 2.6 MPa to about 4.2 MPa.

The source of hydroxyl ions used to catalyze the hydrolysis reaction can be an aqueous solution of ammonia and/or an alkali metal hydroxide and/or an alkaline earth metal hydroxide, with sodium hydroxide being preferred. The amount of the hydroxyl ion source added to the residue stream is controlled so that the molar ratio of hydroxyl ions to hydroxyphenyl groups in the residue stream is from about 0.3:1 to about 0.9:1, such as from about 0.4:1 to about 0.7:1. Thus it is found that advantageous phenol and acetone recoveries can be achieved within these ranges, whereas increasing the hydroxyl/hydroxyphenyl molar ratio above these ranges achieves little or no improvement in recovery and increases caustic usage.

The amount of water added to the residue stream is normally adjusted so that the weight ratio of water to the sum of BPA, BPA isomers, trisphenols and other aromatic heavies in the feed stream is greater than or equal to 2:1, since at water/heavies ratios below 2 it is found that the recovery of phenol and acetone in the hydrolysis reaction is decreased. Generally, the weight ratio of water to the sum of BPA, BPA isomers, trisphenols and other aromatic heavies in the feed stream is from about 2:1 to about 10:1.

The duration of the hydrolysis reaction is generally determined by the degree of phenol and acetone recovery desired. In particular, it is found that advantageous recovery rates in excess of 70%, even in excess of 80% can be achieved with reaction times less than 4 hours, such as from about 2 to about 3 hours. Residence times above these values generally lead to little increase in phenol and acetone recovery. In this respect, the product recoveries are defined as the number of moles of phenolic rings or acetone moieties in the feed minus the number the moles of hydroxyphenyl or acetone moieties in the product divided by the number the moles of hydroxyphenyl or acetone moieties in the feed. For both recoveries, the number of moles of phenol and acetone in the feed are excluded from the calculation.

The invention will now be more particularly described with reference to the Examples and the accompanying drawings.

Example 1

A residue stream was collected from a BPA manufacturing plant having the following composition: 75 weight percent phenol, 17 wt % bisphenol A and isomers thereof, and 8 wt % heavies.

A series of samples were prepared in which 35 g of the residue stream were mixed with 105 g of an 8 wt % sodium hydroxide in water solution so as to produce a plurality of mixtures having a heavies/water weight ratio of 0.1 and an hydroxide/hydroxyphenyl molar ratio of 0.6.

A first set of the resultant mixtures was then heated to various temperatures in the range of 190 to 250° C. for a time of 2 hours and the percentage recovery of phenol and acetone was measured. The results are shown in FIG. 1 and demonstrate that the recovery of each of phenol and acetone increased from about 40% at 190° C. to about 90% at 250° C.

Example 2

Figure 2:
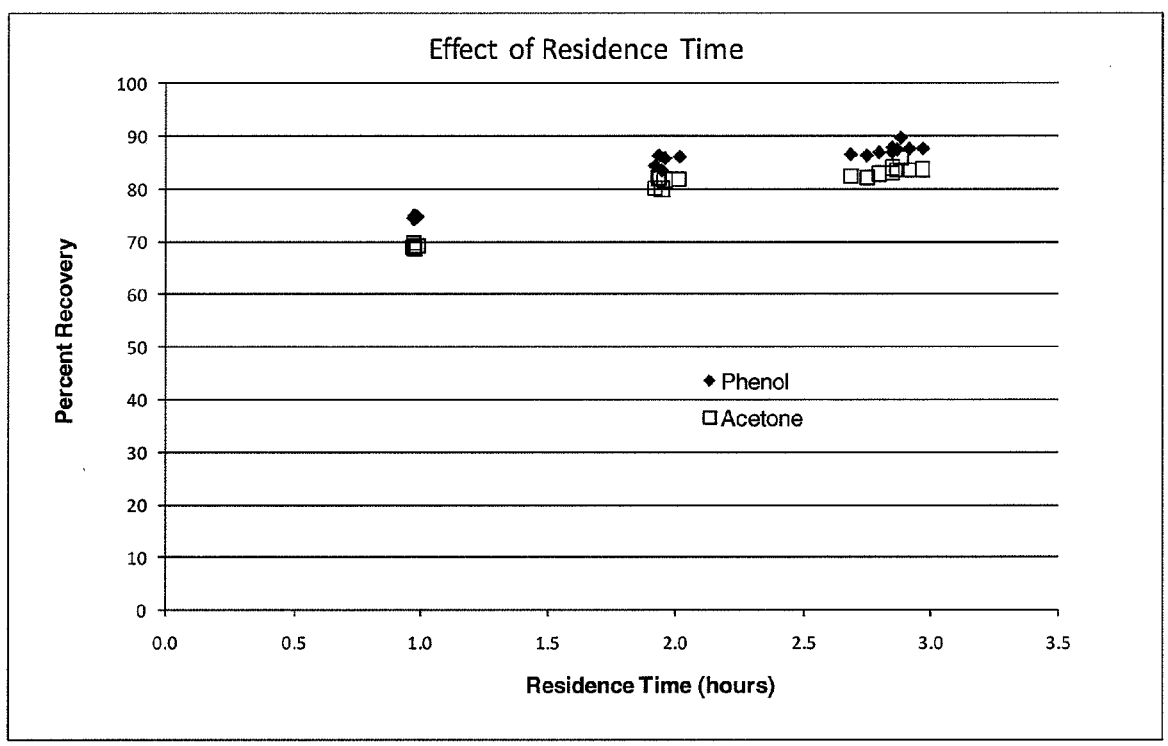
FIG. 2 is a graph of wt % phenol and acetone recovery against residence time at a temperature of 250° C. in the process according to Example 2.

A second set of the samples produced in Example 1 was heated at 250° C. for various times between 1 and 3 hours and the percentage recovery of phenol and acetone was measured. The results are shown in FIG. 2 and demonstrate that the recovery of each of phenol and acetone increased from about 70% for a residence time of 1 hour to about 80% for a residence time of 2 hours. However, little increase in recovery was observed when the residence time was increased to 3 hours.

Example 3

Figure 3:
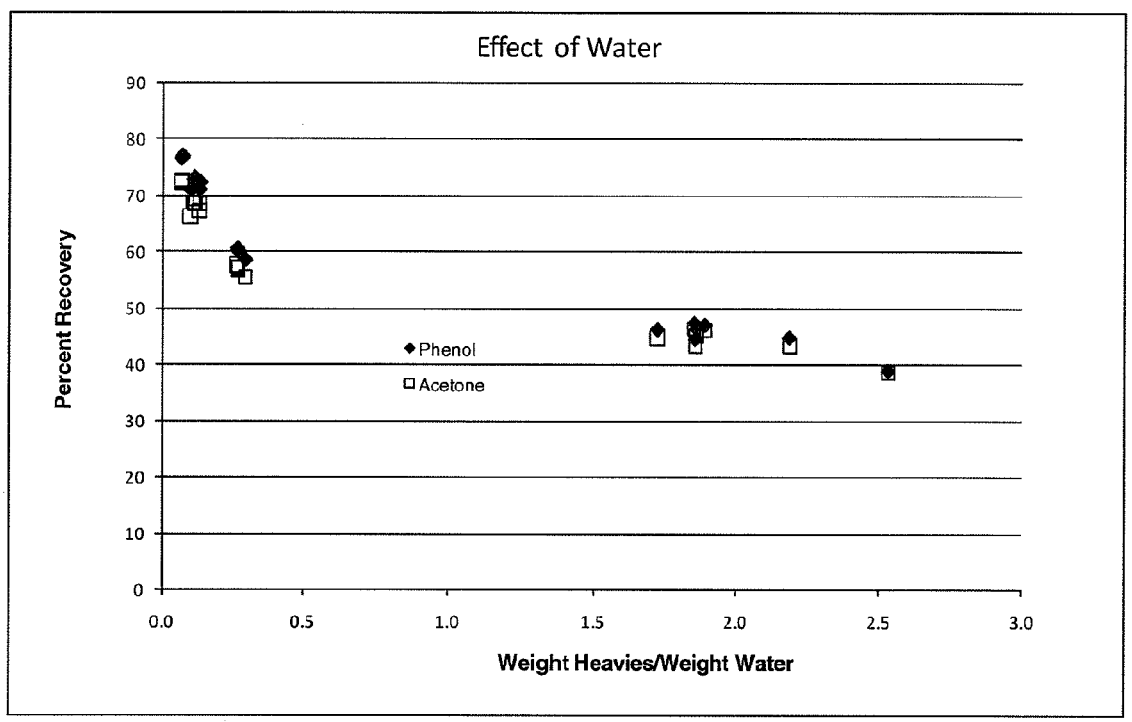
FIG. 3 is a graph of wt % phenol and acetone recovery against heavies to water weight ratio at a temperature of 250° C. in the process according to Example 3.

A further series of samples were prepared in which varying amounts of the residue stream used in Example 1 were mixed with varying amounts of sodium hydroxide in water solutions so as to produce a plurality of mixtures having heavies/water weight ratios varying between of 0.1 and 2.5 and a hydroxide/hydroxyphenyl molar ratio between 0.01 to 0.6. The resultant mixtures were each heated at 250° C. for 2 hours and the percent recovery of phenol and acetone was measured. The results are shown in FIG. 3 and demonstrate that the recovery of each of phenol and acetone decreased from about 70-80% for the mixture having a heavies/water weight ratio of 0.1 to about 50% or less for the mixtures having heavies/water weight ratios in excess of 1.5.

Example 4

Figure 4:
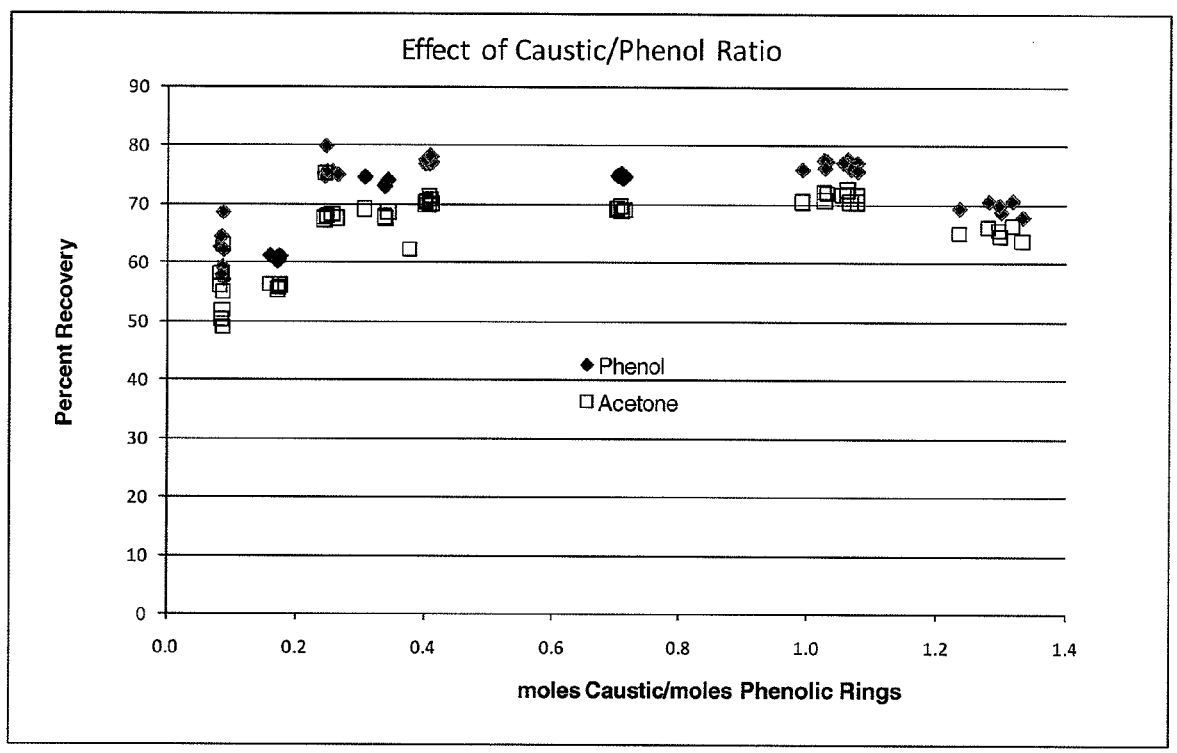
FIG. 4 is a graph of wt % phenol and acetone recovery against molar ratio of hydroxyl ions to hydroxyphenyl groups at a temperature of 250° C. in the process according to Example 4.

A further series of samples were prepared in which 60 g of the residue stream used in Example 1 was mixed with 210 g of varying concentrations of sodium hydroxide in water solutions so as to produce a plurality of mixtures having a heavies/water weight ratio between 0.07 to 0.08 and hydroxide/hydroxyphenyl molar ratios varying between 0.1 and 1.4. The resultant mixtures were each heated at 250° C. for 1 hours and the percent recovery of phenol and acetone was measured. The results are shown in FIG. 4 and demonstrate that the recovery of each of phenol and acetone remained at about 70-80% for the mixtures having hydroxide/hydroxyphenyl molar ratios varying between 0.3 and around 1, but decreased for mixtures having hydroxide/hydroxyphenyl molar ratios above and below these values.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method of recovering phenol and acetone from a feed stream containing bisphenol-A and isomers thereof, the method comprising contacting the feed stream with water and a source of hydroxyl ions under conditions effective to decompose at least part of said bisphenol-A and isomers thereof to phenol and acetone, said conditions including a temperature of about 150° C. to about 300° C., a pressure sufficient to keep the water substantially in the liquid phase at said temperature, and a molar ratio of hydroxyl ions to hydroxyphenyl groups in the residue stream from about 0.3:1 to about 0.9:1.

2. The method of claim 1, wherein said temperature is about 180° C. to about 260° C.

3. The method of claim 1, wherein the molar ratio of hydroxyl ions to hydroxyphenyl groups in said feed stream is from about 0.4:1 to about 0.7:1.

4. The method of claim 1, wherein said contacting is conducted for less than 4 hours.

5. The method of claim 1, wherein said contacting is conducted for about 2 to about 3 hours.

6. The method of claim 1, wherein the feed stream is a residue stream from the production of bisphenol-A, containing unreacted phenol, BPA and isomers thereof, trisphenols and other heavy aromatic compounds.

7. The method of claim 1, wherein the weight ratio of water to the sum of BPA and isomers thereof, trisphenols and other aromatic heavies in the feed stream is greater than or equal to 2:1.

8. The method of claim 1, wherein the weight ratio of water to the sum of BPA and isomers thereof, trisphenols and other aromatic heavies in the feed stream is from about 2:1 to about 10:1.

9. A method of producing bisphenol-A, the method comprising:
    (a) condensing acetone with a molar excess of phenol in the presence of a catalyst under conditions to produce a product stream comprising bisphenol-A and isomers thereof, unreacted phenol, trisphenols and other heavy aromatic compounds;
    (b) recovering part of the bisphenol-A and unreacted phenol from said product stream to leave a residue stream comprising unreacted phenol bisphenol-A and isomers thereof, trisphenols, and other heavy aromatic compounds;
    (c) contacting the feed stream with water and a source of hydroxyl ions under conditions effective to decompose at least part of said residue stream to phenol and acetone, said conditions including a temperature of about 150° C. to about 300° C., a pressure sufficient to keep the water substantially in the liquid phase at said temperature, and a molar ratio of hydroxyl ions to hydroxyphenyl groups in the residue stream from about 0.3:1 to about 0.9:1; and
    (d) recovering phenol and acetone from the effluent stream.

10. The method of claim 8, wherein said temperature is 180° C. to about 260° C.

11. The method of claim 8, wherein the molar ratio of hydroxyl ions to hydroxyphenyl groups in the residue stream is from about 0.4:1 to about 0.7:1.

12. The method of claim 8, wherein weight ratio of water to the sum of BPA and isomers thereof, trisphenols and other aromatic heavies in the residue stream is greater than or equal to 2:1.

13. The method of claim 8, wherein weight ratio of water to the sum of BPA and isomers thereof, trisphenols and other aromatic heavies in the residue stream is from about 2:1 to about 10:1.

14. The method of claim 8, wherein said contacting is conducted for less than 4 hours.

15. The method of claim 8, wherein said contacting is conducted for about 2 to about 3 hours.

* * * * *